United States Patent
Sasing

(10) Patent No.: US 8,992,544 B2
(45) Date of Patent: Mar. 31, 2015

(54) TOOL AND SET SCREW FOR USE IN SPINAL IMPLANT SYSTEMS

(75) Inventor: Jude L. Sasing, Makati (PH)

(73) Assignee: Orthopaedic International, Inc. (PH)

( * ) Notice: Subject to any disclaimer, the term of this patent is extended or adjusted under 35 U.S.C. 154(b) by 832 days.

(21) Appl. No.: 13/159,552

(22) Filed: Jun. 14, 2011

(65) Prior Publication Data

US 2011/0306984 A1 Dec. 15, 2011

Related U.S. Application Data

(60) Provisional application No. 61/354,436, filed on Jun. 14, 2010.

(51) Int. Cl.
*A61B 17/58* (2006.01)
*A61B 17/88* (2006.01)
*A61B 17/86* (2006.01)
*A61B 19/00* (2006.01)

(52) U.S. Cl.
CPC ......... *A61B 17/8888* (2013.01); *A61B 17/8615* (2013.01); *A61B 2019/307* (2013.01)
USPC ....................................................... 606/104

(58) Field of Classification Search
USPC ............ 606/53, 279, 281, 306, 96, 104, 86 A
See application file for complete search history.

(56) References Cited

U.S. PATENT DOCUMENTS

| 7,204,838 | B2 * | 4/2007 | Jackson | 606/270 |
| 7,621,918 | B2 * | 11/2009 | Jackson | 606/86 A |
| 8,123,751 | B2 * | 2/2012 | Shluzas | 606/86 R |
| 8,591,515 | B2 * | 11/2013 | Jackson | 606/86 A |
| 2004/0186478 | A1 * | 9/2004 | Jackson | 606/73 |
| 2006/0276789 | A1 * | 12/2006 | Jackson | 606/61 |
| 2007/0032162 | A1 * | 2/2007 | Jackson | 446/1 |
| 2007/0043358 | A1 * | 2/2007 | Molz et al. | 606/61 |
| 2009/0105718 | A1 * | 4/2009 | Zhang et al. | 606/104 |
| 2010/0114167 | A1 * | 5/2010 | Wilcox et al. | 606/250 |

\* cited by examiner

*Primary Examiner* — David Bates
*Assistant Examiner* — Michael Araj
(74) *Attorney, Agent, or Firm* — Kagan Binder, PLLC

(57) ABSTRACT

The present invention relates to a tool in combination with a set screw for use in spinal implant systems, and more particularly to a tool for the deployment of set screws with a break-off neck portion comprising a handle portion, a stem portion extending from the handle portion, a set screw retaining means, and a driving means extending from the stem portion and disposed opposite the handle portion. The driving means is adapted to allow the installation of the set screw to the bone and applying torque for the shearing of the neck portion thereof, and at the same time is adapted to remove the installed screw portion of the said set screw when needed.

2 Claims, 7 Drawing Sheets ated Patent Application Ser. No. 61/354,436, entitled "A TOOL AND SET SCREW FOR USE IN SPINAL IMPLANT SYSTEMS", filed Jun. 14, 2010, the entire disclosure of which is hereby incorporated by reference as if being set forth herein in its entirety.

TOOL AND SET SCREW FOR USE IN SPINAL IMPLANT SYSTEMS

This Application claims the benefit of priority to U.S. Provisional Patent Application Ser. No. 61/354,436, entitled "A TOOL AND SET SCREW FOR USE IN SPINAL IMPLANT SYSTEMS", filed Jun. 14, 2010, the entire disclosure of which is hereby incorporated by reference as if being set forth herein in its entirety.

TECHNICAL FIELD

The present invention relates in general to spinal implant systems, but more particularly to a tool adapted for the deployment of set screws with a break-off neck portion featuring a means to allow the installation of the set screw to a spinal bone screw or hook and applying torque for the shearing of the neck portion thereof, and at the same time adapted to remove the installed screw portion of the set screw from the bone screw or hook.

BACKGROUND OF THE INVENTION

Existing spinal implant systems employ various instrumentations to secure, adjust and remove the self-limiting set screws to a bone screw or a hook. Tools such as set screw holders, break-off screw drivers, and set screw removal screw drivers are used separately in various stages of the implantation procedure. Such tools are made and dedicated only for a particular stage in the implanting process. Generally, the implantation procedure involves the following steps, namely:

1. Receiving and installing a corresponding set screw to the bone screw or hook;
2. Applying the required amount of torque to the set screw to shear off the head portion thereof and tighten the screw on the bone screw or hook; and
3. Removing the set screw, when required, from the bone screw or hook after the installation thereof.

The present spinal implants systems are expensive, tedious and longer to administer since each of the aforementioned general steps require specific and dedicated tools to achieve the desired objectives.

Although various features have been incorporated to existing instrumentations for implant purposes, a single tool that is simple in its construction and is easy to use is necessary to solve the aforementioned drawbacks and difficulties presented by existing spinal implant systems.

SUMMARY OF THE INVENTION

The proposed invention seeks to simplify and solve the existing tooling problems in present spinal implant systems by providing a single tool and in combination with a self-limiting set screw for spinal implant systems. The tool is dedicated and solely adapted to be used for all the following spinal implant procedures, namely: (a) receiving and installing a corresponding set screw to the bone screw or hook; (b) applying the required amount of tightening torque to the set screw; and finally (c) removing the set screw from the bone screw or hook after the installation thereof. Unlike in existing spinal implant systems, only one tool is used in the procedures for installing, tightening, and removing the set screw from the bone screw or hook.

It is, therefore, the main object of the present invention to provide a single tool in combination with a set screw to solve the technical problem of avoiding the very the tedious procedure of using different tools in the spinal implant system.

More particularly, the present invention provides for a tool with a set screw for use in spinal implant systems, said tool comprising a handle, a stem extending from said handle, a first protrusion extending axially from the end portion of said stem opposite said handle and reduced second protrusion extending axially from said first protrusion, said first and second protrusions being provided with a plurality of adjacent substantially V-shaped projections formed along the surfaces thereof adapted to engage with internal V-shaped notches of said set screw, said stem being provided with at least one flexible arm formed along the lower portion thereof and proximate said first protrusions, said flexible arm having an outwardly directed flange portion formed at the tip thereof to interlock with said set screw, said set screw comprising a body formed with an axial bore and having a head portion, a neck portion and a threaded screw portion extending from said neck portion, said head portion having a internal peripheral notch formed at the upper portion thereof and a plurality of substantially V-shaped internal notches formed along the surface thereof, and said threaded screw portion having an external thread and a plurality of substantially V-shaped internal notches formed along the surface thereof.

These and other objects and advantages of the present invention will become more apparent upon a reading of the ensuing detailed description taken in conjunction with the appended drawings.

DETAILED DESCRIPTION

Figure 1:
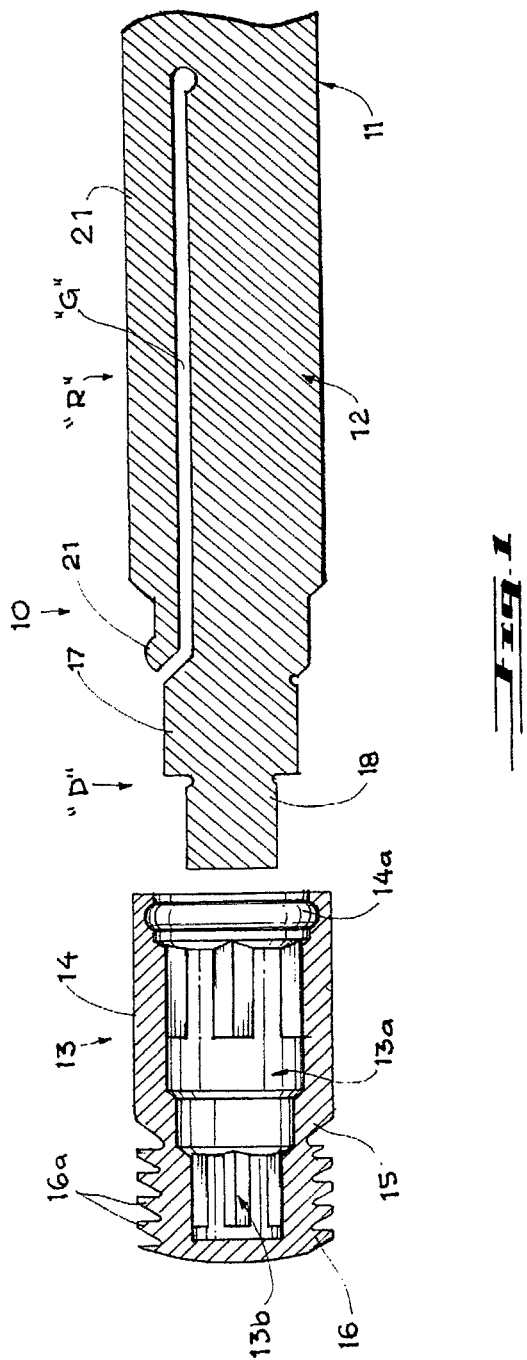
FIG. 1 is a sectional view showing the tool and corresponding set screw of the present invention in detached position.

It is to be understood that the phraseologies and terminologies used herein are for the purposes of description and should not be regarded as limiting.

Referring now to the different views of the drawings, wherein like reference numerals designate the steps, components or elements throughout the ensuing enabling description, the present invention provides for a tool for use in spinal implant systems adapted for the deployment of set screws with a break off head designated as 10.

Figure 3:
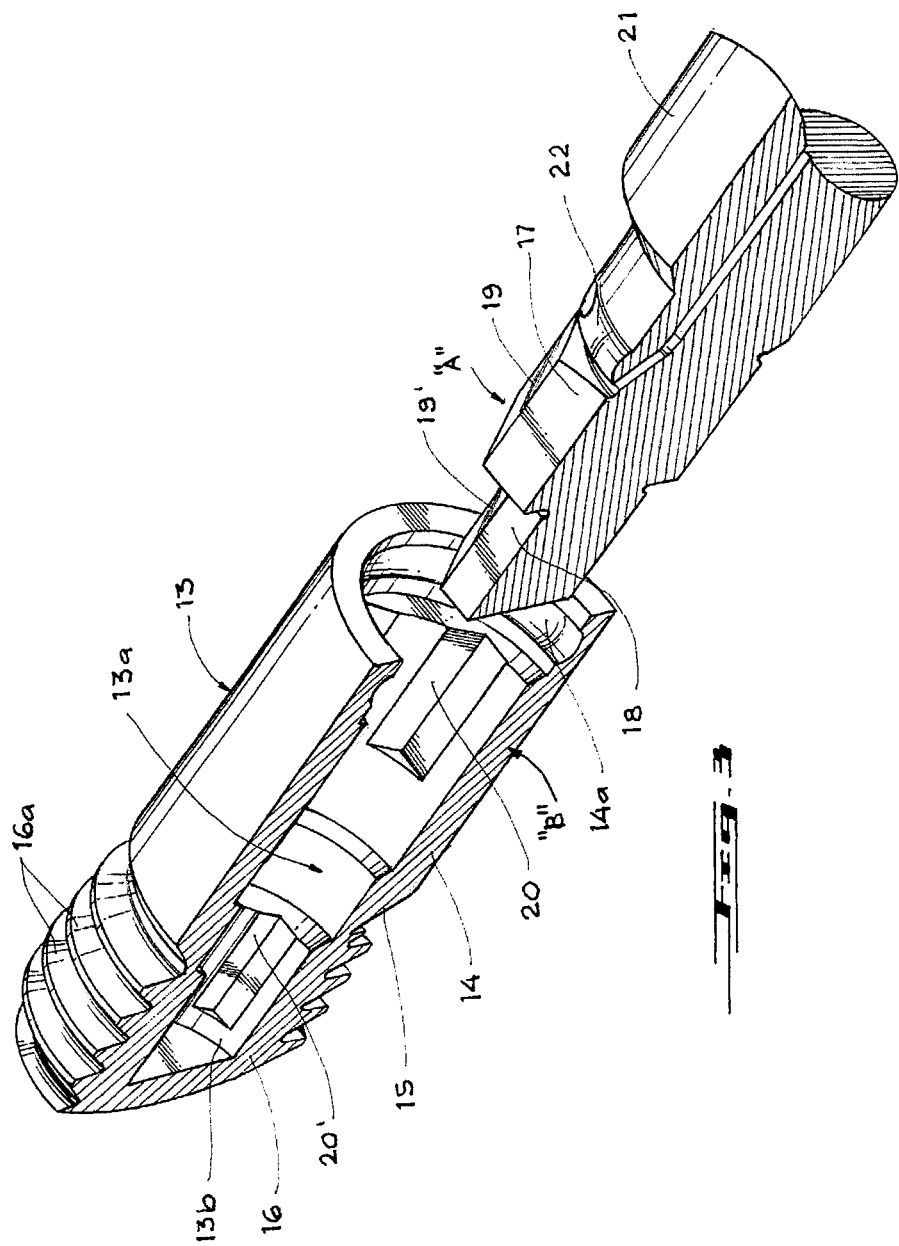
FIG. 3 is a sectional perspective view of the tool and corresponding set screw of the present invention.
Figure 4:
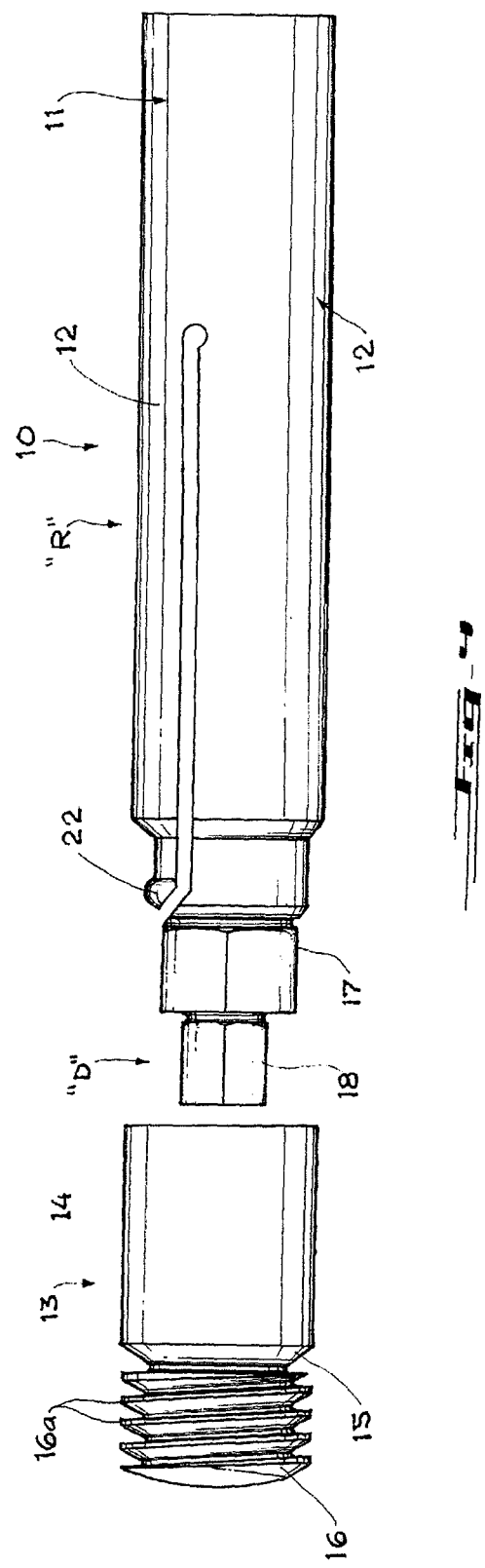
FIG. 4 is another side view showing the tool and corresponding set screw of the present invention.
Figure 5:
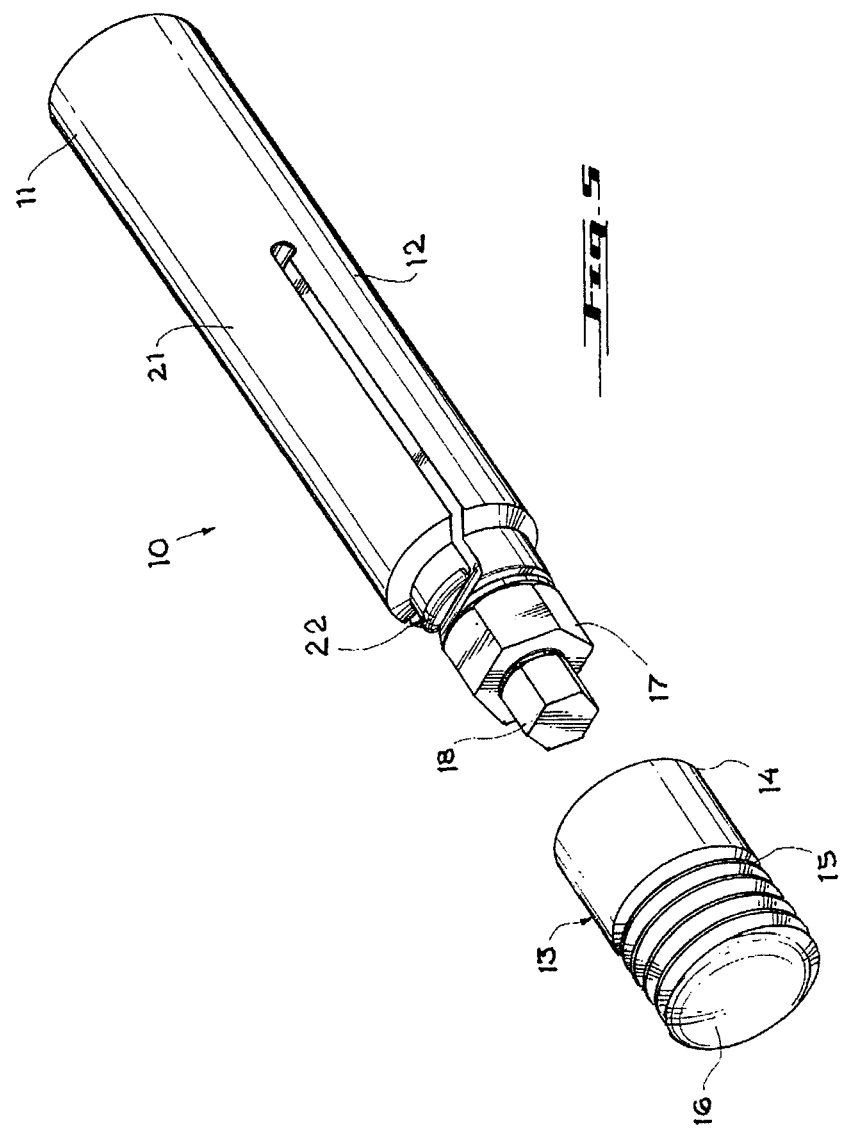
FIGS. 5 and 6 are perspective views showing the tool and corresponding set screw of the present invention.
Figure 6:
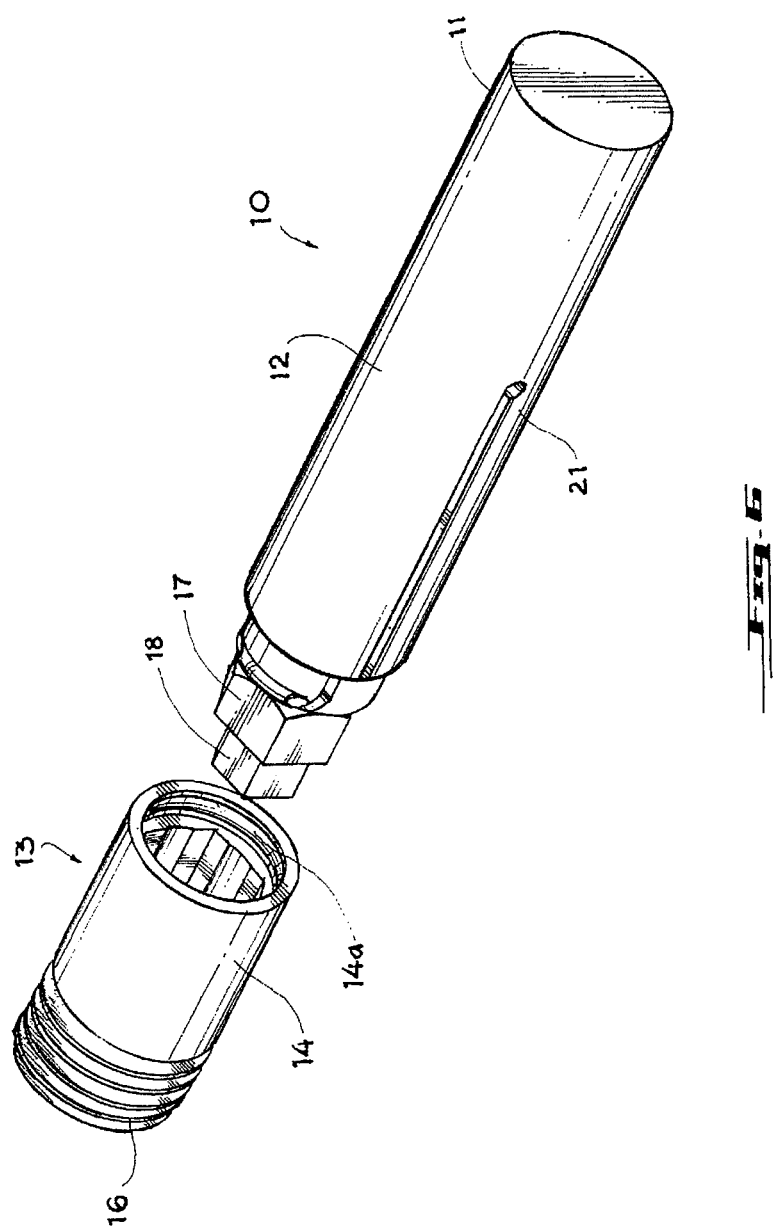

As shown in FIGS. 1 & 3, the tool 10 comprises a handle portion 11, a stem portion 12 extending from the handle portion 11 and a driving means "D" provided on the tool 10, particularly extending from the stem portion 12 and disposed opposite handle portion 11. A corresponding set screw 13 is provided to engage with the tool 10 to connect the bone screw or hook and spinal rod in the implant system, and comprising a head portion 14, a break-off neck portion 15 and a preferably reduced threaded screw portion 16 extending from the head portion 14. Set screw 13 is formed by an axial bore 13*a* and extending to a reduced axial bore 13*b* at the screw portion 16. Screw portion 16 is also formed with external screw thread 16*a* and head portion 14 is formed with an internal peripheral notch 14*a* formed at the upper portion thereof.

Figure 2:
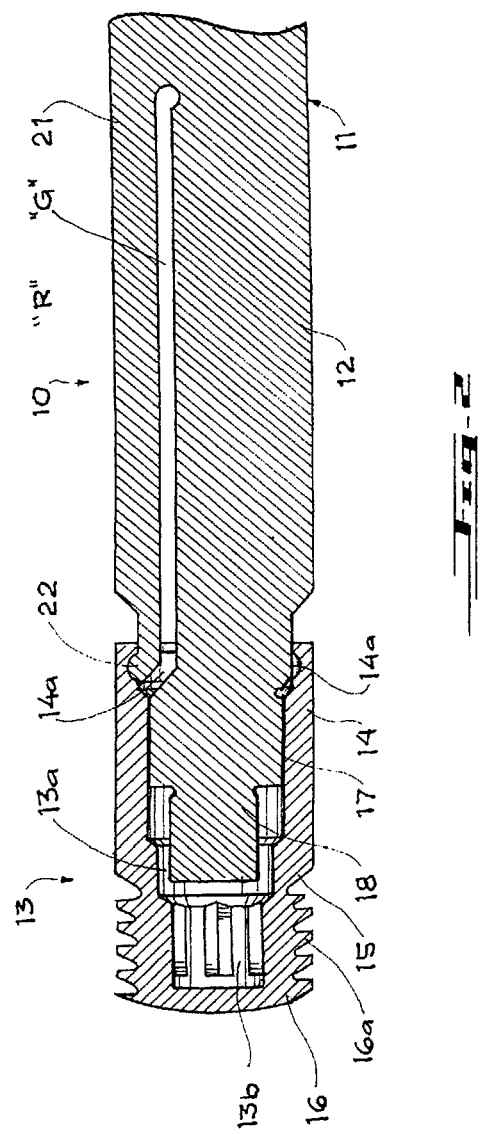
FIG. 2 is a sectional view showing the tool and corresponding set screw of the present invention in engaged position.

Referring now to FIG. 2, the driving means "D" is adapted to allow the installation of the set screw 13 to the bone screw or hook and applying torque for the shearing of the neck portion 15 thereof, and simultaneously adapted to remove the installed screw portion 16 on the bone screw or hook after the installation thereof.

Driving means "D" comprises a first protrusion 17 extending axially from the end portion of the stem portion 12 opposite the handle portion 11, and a reduced second protrusion 18 extending axially from the first protrusion 17. The diameter of the first protrusion 17 is such that it is sized to conform within the inner diameter of axial bore 13a, and likewise the second protrusion 18 has a diameter sized to conform to the inner diameter of axial bore 13b of the set screw 13. The first and second protrusions 17 & 18 are further provided with corresponding first locking means "A", and a corresponding second locking means "B" is provided along the axial bores 13a & 13b of set screw 13. The first and second locking means "A" and "B" are provided to engage the tool 10 to the set screw 13. Furthermore, a retaining means "R" is provided on the stem portion 12 to allow the handling and installation of the set screw 13 on a bone screw or hook prior to shearing of the neck portion 15 thereof.

As shown in the drawings, particularly in FIG. 3, the first locking means "A" comprises a plurality of adjacent substantially V-shaped projections 19, 19' formed along the surfaces of the first and reduced second protrusions 17 & 18, and the second locking means "B" comprises the corresponding plurality of adjacently disposed substantially V-shaped notches 20, 20' formed along the internal surfaces of head portion 14 and the screw portion 16 of the set screw 13, respectively The retaining means "R" comprises at least one flexible arm 21 formed proximate along the side portion of the stem portion 12 defining a gap "G" between the stem portion 12 and the flexible arm 21, and flexible arm 21 is also disposed proximate the first protrusion 17. The flexible arm 21 has an outwardly directed flange portion 22 formed at the tip thereof. The flange portion 22 is adapted to interlock with the peripheral notch 14a of the head portion 14 when the set screw 13 is to be installed in the bone screw or hook. The gap "G" allows the flexible arm 21 to be flexed inwardly towards the side of the stem portion 12 when the flange portion 22 is interlocked with the peripheral notch 14a.

As shown in FIGS. 1 & 3, first protrusion 17 is substantially larger than second protrusion 18. It is known in the art that the tightening torque for a set screw is higher than the loosening torque. The larger dimensions of protrusion 17 allow it to shear off the head portion 14 of setscrew 13 at the break-off neck portion 15. The smaller dimensions of second protrusion 18 prevent it from engaging the V-shaped notches 20, protecting it from excessive torque during tightening. In existing implant systems, the tool used for tightening the set screw by a break-off feature usually cannot be used for loosening the set screw because of its large dimensions. On the other hand, the tool used for loosening the set screw cannot be used for tightening by break-off because it is not strong enough due to its small dimensions.

In operation, the tool 10 is first engaged to the set screw 13 by inserting the first protrusion 18 within the axial bore 13a of the head portion 14 as shown in FIG. 2. The flange portion 22 of the flexible arm 21 is adapted to seat on the peripheral notch 14a of the head portion 14 as to retain the set screw 13 in a stable and controllable manner in preparation for its surgical attachment to the bone screw or hook. The first protrusion 17 is interlocked within the axial bore 13a by the engaging of the V-shaped projections 19 with the corresponding V-shaped notches 20. In this particular position, the reduced second protrusion 18 is also held within the axial bore 13a as shown in FIG. 2, but is not engaged to any portion of set screw 13. The engaging relationship of the V-shaped projections 19 with the corresponding V-shaped notches 20 easily facilitates connecting the set screw to the bone screw or hook, and further imparts a controlled amount of torque in breaking the neck portion 15 of the set screw 13. After installing the set screw 13, the head portion 14 is sheared from the screw portion 16 and the same is easily removed from the tool 10 by inwardly pressing the flexible arm 21 to release the flange portion 22 away from the peripheral notch 14a and, finally, pulling the head portion 14 from the tool 10. Alternatively, the head portion 14 can be removed from the tool 10 by exerting sufficient pulling force without pressing the flexible arm 21. The installed screw portion 16 can be later removed if necessary from the bone screw or hook by using the same tool 10. To uninstall the screw portion 16, the reduced second protrusion 18 of the tool 10 is simply engaged with the axial bore 13b thereof via engaging the V-shaped projections 19' with the V-shaped notches 20'.

Figure 7:
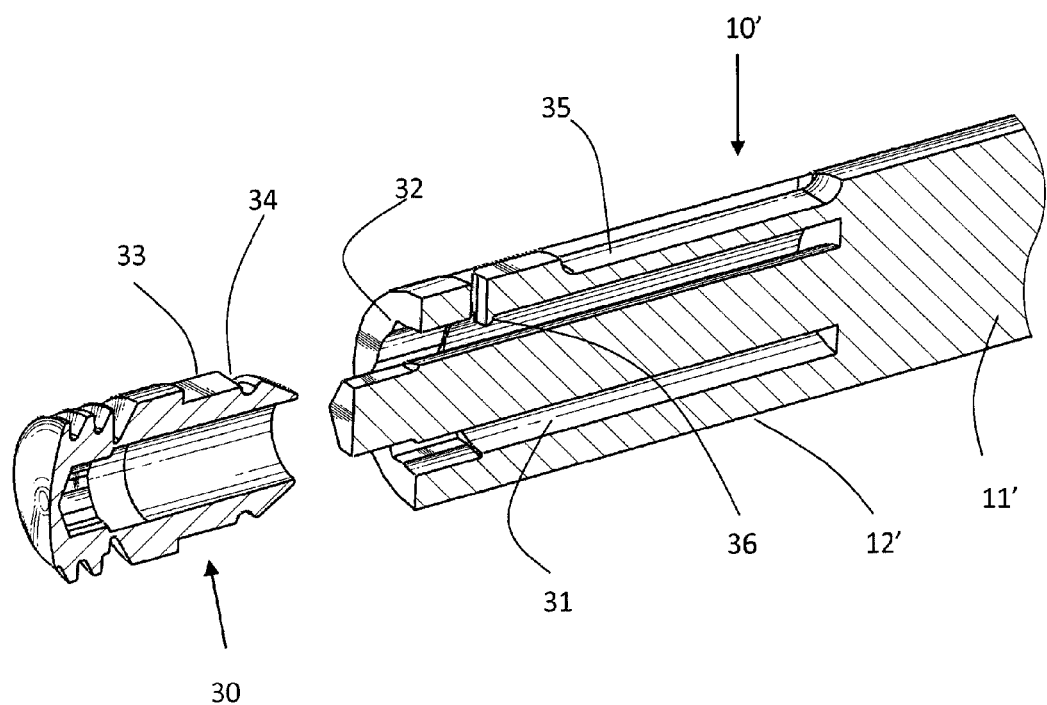
FIG. 7 is a sectional view showing an alternative embodiment of the present invention.

In another embodiment according to the present invention as shown in FIG. 7, the first protrusion 17 of FIG. 3 is replaced by a cavity 31 extending inward from the end portion of stem portion 12' opposite the handle portion 11'. Said cavity 31 is provided with a plurality of adjacent substantially V-shaped internal notches 32 formed along the surface thereof to engage with corresponding V-shaped projections 33 on setscrew 30.

Set screw 30 is further provided with an external peripheral notch 34 formed at the upper portion thereof. Correspondingly, tool 10' is provided with a flexible arm 35 with an inwardly facing flange 36 formed at the tip thereof. The flange portion 36 is adapted to interlock with the peripheral notch 34 when the set screw 30 is to be installed in the bone screw or hook.

The present invention also discloses a method for installing, tightening and loosening a set screw on a spinal bone screw or hook, using a single tool, more particularly, the herein tool and set screw as previously described. The method comprising the steps of: providing a tool having a handle portion and a stem portion extending from said handle portion, said tool having a retaining means and a driving means for a set screw;

providing a set screw having an axial bore, a head portion, a break-off neck portion and a threaded screw portion extending from said neck portion; attaching and retaining said set screw on said tool; tightening the set screw on a spinal bone screw or hook by shearing off the head portion of said set screw at the break-off neck portion using said tool; removing the sheared off head portion from said tool; and loosening, when needed, the threaded screw portion of said set screw from the spinal bone screw or hook using said tool.

Additional advantages and modifications of the present invention will readily occur to those skilled in the art in view of these teachings. The present invention in its broader aspects is not limited to the specific details, representative contrivances, and illustrative examples shown and described herein. Accordingly, various modifications may be made without departing from the spirit and scope of the general concept as defined in the appended claims and their equivalents.

The invention claimed is:

1. In combination, a tool with a set screw for use in spinal implant systems, comprising:

a tool having a handle portion and a stem portion extending from said handle portion;

a set screw having an axial bore, a head portion, a break-off neck portion, a threaded screw portion extending from said neck portion, and an internal peripheral notch formed at an upper portion of the head portion;

a retaining means provided on said stem portion to allow handling and installation of said set screw, said retaining means comprising at least one flexible arm formed proximate the side portion of said stem portion defining a gap therebetween, said at least one flexible arm having an outwardly directed flange portion formed at the tip thereof, said flange portion being adapted to interlock with said internal peripheral notch of the head portion when said set screw is to be installed in the bone screw or hook; and a driving means provided on said tool to allow the installation of said set screw to a bone screw or hook, apply torque for the shearing of the neck portion of said set screw, and remove the installed screw portion of said set screw on said bone screw or hook.

2. In combination, a tool with a set screw for use in spinal implant systems, comprising:

a tool having a handle portion and a stem portion extending from said handle portion;

a set screw having an axial bore, a head portion, a break-off neck portion, a threaded screw portion extending from said neck portion, and an external peripheral notch formed at an upper portion of the head portion;

a retaining means provided on said stem portion to allow handling and installation of said set screw, said retaining means comprising at least one flexible arm formed along the side portion of said stem portion, said flexible arm having an inwardly directed flange portion formed at the tip thereof, said flange portion being adapted to interlock with said external peripheral notch of the head portion when said set screw is to be installed in the bone screw or hook; and a driving means provided on said tool to allow the installation of said set screw to a bone screw or hook, apply torque for the shearing of the neck portion of said set screw, and remove the installed screw portion of said set screw on said bone screw or hook.

* * * * *